United States Patent [19]

Ohi et al.

[11] Patent Number: 4,946,467

[45] Date of Patent: Aug. 7, 1990

[54] SURGICAL SUTURE

[75] Inventors: Shigeo Ohi; Masakazu Suzuki; Toru Yamamoto, all of Ayabe, Japan

[73] Assignee: Gunze Limited, Ayabe, Japan

[21] Appl. No.: 320,529

[22] Filed: Mar. 8, 1989

[30] Foreign Application Priority Data

Mar. 14, 1988 [JP] Japan .............................. 63-34397[U]

[51] Int. Cl.⁵ .............................................. A61B 17/00
[52] U.S. Cl. .................................................... 606/228
[58] Field of Search ....................... 128/335.5; 606/228

[56] References Cited

U.S. PATENT DOCUMENTS

| | | | |
|---|---|---|---|
| 4,014,973 | 3/1977 | Thompson | 128/335.5 |
| 4,043,344 | 8/1977 | Landi et al. | 128/335.5 |
| 4,362,162 | 12/1982 | Nakajima et al. | 128/334 R |
| 4,461,298 | 7/1984 | Shalaby et al. | 128/335.5 |
| 4,506,672 | 3/1985 | Bichon | 128/335.5 |
| 4,546,769 | 10/1985 | Planck | 128/335.5 |
| 4,550,730 | 11/1985 | Shalaby et al. | 128/335.5 |

FOREIGN PATENT DOCUMENTS

| | | |
|---|---|---|
| 120113 | 8/1981 | Japan . |
| 120114 | 8/1981 | Japan . |
| 63148341 | 9/1981 | Japan . |
| 57-48933 | 3/1982 | Japan . |
| 57-48934 | 3/1982 | Japan . |
| 2081756A | 6/1981 | United Kingdom . |
| 2082213A | 6/1981 | United Kingdom . |

Primary Examiner—Randall L. Green
Assistant Examiner—Gary Jackson
Attorney, Agent, or Firm—Armstrong, Nikaido, Marmelstein, Kubovcik & Murray

[57] ABSTRACT

A suture comprising a core of at least one synthetic fiber filament yarns, and a covering layer formed of a plurality of silk strands and sheathing the core, the core and the covering layer having substantially the same elongation at break. The filament yarns have increased modulus of elasticity and increased breaking strength to thereby give the suture improved breaking strength and also have enhanced rigidity to render the suture highly amenable to the correction of its deformation and easier to handle.

10 Claims, 2 Drawing Sheets

SURGICAL SUTURE

BACKGROUND OF THE INVENTION

1. Field of Invention

The present invention relates to sutures for use in surgery.

2. Description of the Prior Art

Sutures of silk have long been known and used for various surgical applications. Conventional sutures are of various types and include those prepared by twisting, braids formed by plaiting, and braids having a core. The known suture is made of silk only and therefore has the drawback of being low in stiffness and having very poor ability to restore itself when deformed. For example, the suture wound on a reel remains helically curled when unwound therefrom and is difficult to straighten to a corrected form. The same difficulty is also encountered with the suture wound around a paper core.

If the suture used is as curled the suture will coil around the arm or hand of the surgeon or hang down in a helical form due to its excessive flexibility and causes great frustration to the surgeon.

To overcome this problem, we have proposed a suture comprising a core of synthetic fiber filament yarn and a braid or the like of silk strands covering the core (Japanese Utility Model Application No. 41670/1987). The proposed suture is given suitable flexibility due to the appropriate rigidity of the filament yarn as afforded by doubled polyester filament strands in combination with the flexibility of the silk strands covering the yarn, whereby the suture is made amenable to the correction of its deformation such as the curl due to winding so as to be easily handled. Furthermore, the suture has a higher breaking strength than those consisting solely of silk strands owing to the presence of the core of synthetic fiber filament yarn. However, the suture still remains to be improved since there is a demand for sutures having higher strength.

SUMMARY OF THE INVENTION

The main object of the present invention is to provide a surgical suture meeting this demand, and more particularly a suture which has a suitable flexibility and high amenability to the correction of deformation such as the curl due to winding on a reel and is easy to handle and which further has an exceedingly high breaking strength.

To fulfill the above object, the present invention provides a surgical suture characterized in that the suture comprises a core of at least one synthetic fiber filament yarn, and a covering layer formed of a plurality of silk strands and sheathing the core, the core and the covering layer having substantially the same elongation at break.

The core can be formed of a plurality of synthetic fiber filament yarns extending in parallel to one another and each having substantially the same elongation at break as the covering layer.

Furthermore, the core can be formed of single-twisted or plied filament yarns of synthetic fiber and made to have substantially the same elongation at break as the covering layer.

Furthermore, the core can be formed by plaiting a plurality of synthetic fiber filament yarns and made to have substantially the same elongation at break as the covering layer.

The covering layer can be formed by plaiting the plurality of silk strands and made to have substantially the same elongation at break as the core.

The synthetic fiber filament yarn can be made of any of various materials such as nylon, polyester, polypropylene and acrylic, among which polyester which has high breaking strength per denier is especially desirable from the viewpoint of giving improved strength to the suture.

The suture of the present invention has a suitable flexibility due to the rigidity of the core of synthetic fiber filament yarn and because of the flexibility of the covering layer of silk strands, and is thereby given high amenability to the correction of deformation such as the curl due to winding on reels and made easy to handle, hence outstanding advantages. The suture has another advantage; that it is readily deformable to a form suited to suturing during surgery. These great advantages appear attributable also to the fact that slippage occurs more smoothly between the synthetic fiber filament yarn core and the silk strand covering layer than between silk strands.

In the case of the suture already proposed (Japanese Utility Model Application No. 41670/1987) comprising a core of synthetic fiber filament yarn, the filament yarn generally has a higher elongation at break than the silk strands, so that when the suture is stretched under tension, the silk strands reach the limit of elongation (elongation at break) and break first. The force thereafter acts only on the filament yarn to break the yarn. Consequently, the overall breaking strength of the suture is lower than the sum of the individual breaking strengths of the yarn and the silk strands. According to the invention, on the other hand, the core of synthetic fiber filament yarn has substantially the same elongation at break as the covering layer of silk strands, with the result that when the suture breaks under tension, both the core and the covering layer break at the same time. Thus, the sum of the individual breaking strengths of the two is substantially equal to the overall breaking strength of the suture. In this case, synthetic fiber filaments increase in modulus of elasticity as they are made smaller in elongation at break by adjustment through thermal drawing. Accordingly, when the suture comprising such synthetic fiber filaments is compared with the suture comprising usual synthetic fiber filaments, the tensile force acting on the suture when the silk strands are stretched to break is greater on the former suture than on the latter by an amount corresponding to the increase in the modulus of elasticity. Thus, the former suture has a corresponding higher breaking strength. Moreover, the suture has further increased breaking strength because the synthetic fiber filament has higher breaking strength with a decrease in elongation at break. Because of the improved strength, sutures of small diameter are usable for wider application and are advantageous in avoiding injuries to the tissues of the human body to be sutured.

The reduction in the elongation at break gives somewhat increased rigidity to synthetic fiber filaments, makes them more suitable to use and is advantageous in facilitating correction of the deformation of the suture rendering the suture handleable with greater ease.

In the case where the core is formed of synthetic fiber filament yarns extending substantially parallel to one another, it is desirable that the filament yarns be at least 18% to not greater than 24%, more preferably at least 19% to not greater than 21%, in elongation at break because silk strands are generally 18 to 19% in elongation at break and exhibit an elongation at break of 18 to 24%, usually 19 to 21%, when formed into a covering layer by plaiting and so on.

When the core is prepared from synthetic fiber filament yarns by single twisting, plying or plaiting, the core thus formed is adapted to have the same elongation at break as the covering layer, and the elongation is suitably determined in view of twisting or plaiting density, strength, etc.

When the suture to be obtained has a relatively large size of USP2-0 or greater, it is especially desirable to form the core by plying the yarns so that the first twist and the final twist are in opposite directions to offset the torques due to the twists. For sutures of relatively small size of USP3-0 or smaller, single twisting achieves satisfactory results. Although the number of twists for the core is preferably greater to give improved breaking strength to the suture, the filament yarns may be loosely twisted with about 20 to about 50 T/m when made into a compacted ply.

To assure facilitated correction of deformation and improved breaking strength, it is desirable for the suture to have the core in a greater proportion as will become apparent from the following embodiments, especially from the results given in Table 1.

The present invention will become more apparent from the embodiments to be described below with reference to the accompanying drawings.

DETAILED DESCRIPTION OF INVENTION

Embodiment 1

Silk strands were each prepared from two scoured silk yarns substantially of 27 denier (median of fineness values involving usual variations) by twisting the yarns together in S direction at about 300 T/m (s27 Naka/2). Silk strands of another type were also prepared each from two silk yarns, the same as those used above, by twisting the yarns together in Z direction at about 300 T/m (z27 Naka/2). A plied yarn serving as a core was prepared by twisting together eight polyester filament yarns (product of Teijin Limited, T300s, 20 denier, composed of 6 filaments, 19% in elongation at break) in S direction at 200 T/m to obtain a twisted unit, and twisting three such twisted units together in Z direction at 137 T/m. The core thus obtained was about 20% in elongation at break. The core was then sheathed with a covering layer by arranging the two types of silk strands alternately on a braiding machine and plaiting the strands, 16 in total number, into a braid at a density of 26 stitches/cm, whereby a suture of USP1-0 in size was obtained. The covering layer formed was about 20% in elongation at break.

Figure 1:
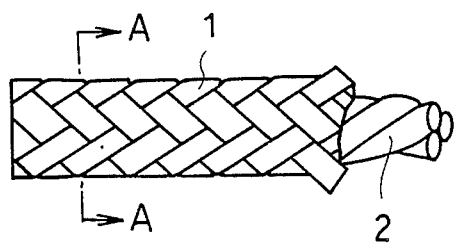
FIG. 1 is a perspective view partly broken away showing a suture embodying the invention.
Figure 2:
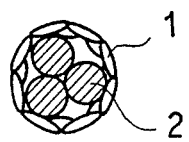
FIG. 2 is a view in section taken along the line A—A in FIG. 1.

The structure of the suture obtained is shown in FIG. 1, in which indicated at 1 is the covering layer formed by plaiting the silk strands, and at 2 is in the core of plied polyester yarn.

The suture prepared in this way had a breaking strength of 2.92 kgf which was 11% higher than that of conventional sutures made of silk yarns only and having the same size. The suture had suitable flexibility (i.e. suitable stiffness), was highly amenable to deformation such as curling and can easily be handled free of trouble. Embodiment 2

Figure 3:
FIG. 3 is a perspective view showing a core of another embodiment.

A single twist yarn serving as a core 2' as shown in FIG. 3 was prepared from three polyester filament yarns (product of Toray Industries, Inc., S200, 20 denier, composed of 6 filaments, 19% in elongation at break) by twisting the yarns together in S direction at 200 T/m. The core obtained was about 19% in elongation at break. The core 2' was then sheathed with a covering layer which was formed in the same manner as in Embodiment 1 by plaiting twelve silk strands into a braid at a density of 29 stitches/cm, whereby a suture of USP4-0 in size was obtained. The covering layer was about 19% in elongation at break.

The suture thus obtained and having a small size also exhibited excellent characteristics like the suture of Embodiment 1.

Other Embodiments

Sutures of varying sizes were prepared in the same manner as above and tested in comparison with conventional sutures. The results are shown in Table 1, in which the sutures of USP1-0 and USP4-0 in size were made of materials different from those of Embodiments 1 and 2. Accordingly, these sutures were slightly different from the above sutures in the results achieved.

TABLE 1

|  | USP size | 2 | 1 | 1-0 | 2-0 | 3-0 | 4-0 | 5-0 | 6-0 |
|---|---|---|---|---|---|---|---|---|---|
| Invention | Number of component strands of covering layer | 16 | 16 | 16 | 16 | 12 | 12 | 8 | 6 |
|  | Core ratio (%) | 47 | 33 | 33 | 33 | 20 | 20 | 11 | 14 |
|  | Elongation of break (%) | 27.8 | 25.0 | 23.7 | 22.2 | 20.3 | 20.0 | 19.4 | 18.5 |
|  | Breaking strength (kgf) | 6.05 | 3.88 | 2.92 | 2.27 | 1.48 | 0.95 | 0.58 | 0.30 |
|  | Flexibility (cm) | 18.5 | 17.5 | 17.0 | 17.0 | 16.0 | 15.5 | 12.0 | 11.0 |
| Prior Art A | Breaking strength (kgf) | 5.68 | 3.76 | 2.86 | 2.18 | 1.41 | 0.91 | 0.54 | 0.28 |
| Prior Art B | Number of component strands of covering layer | 16 | 16 | 16 | 16 | 12 | 12 | 8 | 6 |
|  | Core ratio (%) | 15 | 15 | 15 | 15 | 4 | 4 | 0 | 0 |
|  | Elongation at break (%) | 29.9 | 27.1 | 25.2 | 23.8 | 22.4 | 21.8 | 20.2 | 19.1 |
|  | Breaking strength (kgf) | 4.94 | 3.50 | 2.79 | 2.04 | 1.30 | 0.83 | 0.46 | 0.25 |
|  | Flexibility (cm) | 16.0 | 15.0 | 1.5.5 | 15.0 | 14.0 | 11.5 | 9.5 | 8.0 |

With reference to Table 1, the core ratio is the ratio of the core to the entire suture in weight as expressed in percentage. The flexibility was determined according to the method of JIS L-1096A. Prior Art (prior-art suture)

A was prepared in the same manner as the suture of the invention except that a usual polyester filament yarn (24% in elongation at break) was used as the core. Prior Art (prior-art suture) B had a silk yarn as the core.

Figure 4:
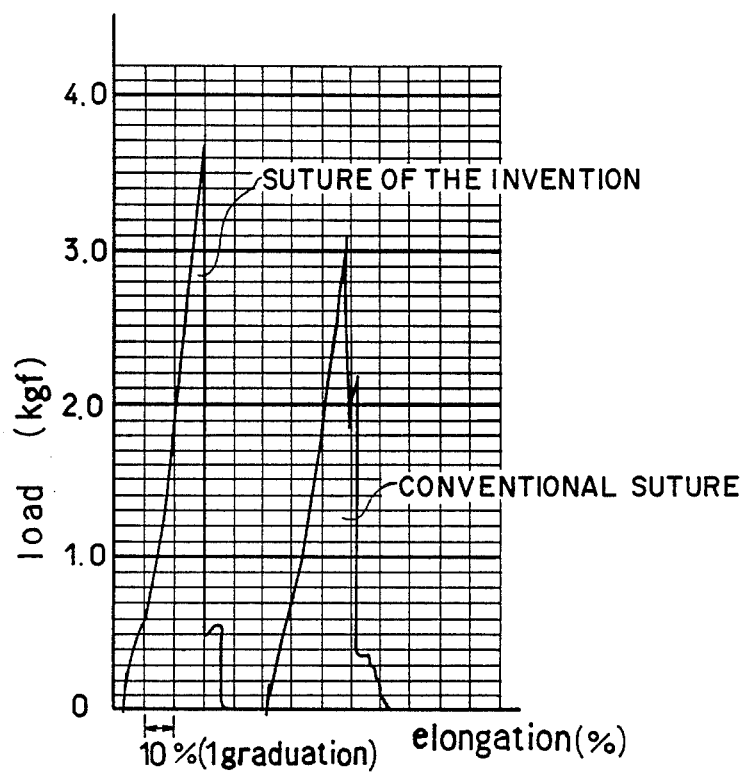
FIG. 4 is a graph showing the relationship between the load and the elongation, as determined for the suture of the invention and a conventional suture and involving a break.

The suture of the invention and a conventional suture comprising a core of usual synthetic fiber filament yarn, both USPI in size, were subjected to a tensile test. FIG. 4 is a graph showing the results. The graph reveals that the suture of the invention has exceedingly higher breaking strength (peak value). The graph also shows that with the conventional suture, the descending line representing a break has an intermediate peak, which indicate that the break involves a time lag between the core and the covering layer. With the suture of the invention, the descending line extends downward almost straight, indicating that the core and the covering layer broke at the same time.

When actually used for operations by surgeons, the sutures of the above embodiments were evaluated as being highly amenable to the correction of curls and like deformations, suitably flexible (suitably stiff), easy to handle to assure an efficient operation and free of any break during handling even when of a reduced size.

The suture of the invention is not limited to the foregoing embodiments but can be modified variously within the scope of the invention defined in the appended claims.

We claim:

1. A surgical suture characterized in that the suture comprises a core of at least one synthetic fiber filament yarn, and a covering layer formed of a plurality of silk strands and sheathing the core, the core and the covering layer having substantially the same elongation at break.

2. A suture as defined in claim 1 wherein the core is formed of a plurality of synthetic fiber filament yarns extending substantially in parallel to one another and each having substantially the same elongation at break as the covering layer.

3. A suture as defined in claim 2 wherein each of the filament yarns is at least 18% to not greater than 24% in elongation at break.

4. A suture as defined in claim 1 wherein the core is formed of a plurality of twisted synthetic fiber filament yarns and made to have substantially the same elongation at break as the covering layer.

5. A suture as defined in claim 4 wherein the synthetic fiber filament yarns are single-twisted.

6. A suture as defined in claim 4 wherein the synthetic fiber filament yarns are plied.

7. A suture as defined in claim 5 which is 9—0 to 3—0 in USP size.

8. A suture as defined in claim 6 which is 2—0 to 10 in USP size.

9. A suture as defined in claim 1 wherein the core is formed of a plurality of braided synthetic fiber filament yarns and made to have substantially the same elongation at break as the covering layer.

10. A suture as defined in claim 1 wherein the plurality of silk strands are braided to form the covering layer and made to have substantially the same elongation at break as the core.

* * * * *